United States Patent [19]
Christgau et al.

[11] Patent Number: 5,707,847
[45] Date of Patent: Jan. 13, 1998

[54] ENZYME EXHIBITING PECTIN METHYLESTERASE ACTIVITY

[75] Inventors: Stephan Christgau, Gentofte; Lene Venke Kofod, Ugerløse; Lene Nonboe Andersen, Birkerød; Sakari Kauppinen, Copenhagen N; Hans Peter Heldt-Hansen, Virum; Gitte Budolfsen, Frederiksberg; Henrik Dalbøge, Virum, all of Denmark

[73] Assignee: Novo Nordisk A/S, Bagsvaerd, Denmark

[21] Appl. No.: 535,230

[22] PCT Filed: Apr. 28, 1994

[86] PCT No.: PCT/DK94/00173

§ 371 Date: Nov. 2, 1995

§ 102(e) Date: Nov. 2, 1995

[87] PCT Pub. No.: WO94/25575

PCT Pub. Date: Nov. 10, 1994

[30] Foreign Application Priority Data

Apr. 30, 1993 [DK] Denmark ............... 0487/93
Oct. 28, 1993 [DK] Denmark ............... 1217/93

[51] Int. Cl.⁶ ............... C12N 9/18; C12N 9/16
[52] U.S. Cl. ............... 435/197; 435/196
[58] Field of Search ............... 435/196, 197

[56] References Cited

U.S. PATENT DOCUMENTS 4,200,694  4/1980  Ishii et al. ............... 435/101
5,413,937  5/1995  Bridges et al. ............... 435/320.1

FOREIGN PATENT DOCUMENTS 0 388 593  9/1990  European Pat. Off.

OTHER PUBLICATIONS

Dialog, file 55: Biosis Preview.
Khan, N., et al. Gene., vol. 106, pp. 71–77 (1991).
Markovic, O., et al., Biologia, vol. 44, No. 12, pp. 1185–1189 (1989).
Abstract –PCT WO 93/13212.
Abstract –PCT WO 93/09683.
Van Rijssel, M., et al., Applied and Environmental Microbiology, vol. 59, No. 3, pp. 828–836 (1993).
Khanh, N., et al., Nucleic Acids Research, vol. 18, No. 14, p. 4262 (1990).
Khanh, N., et al., Biotechnology Letters, vol. 14, No. 11, pp. 1047–1052, (1992).
Markovic, O., et al., Protein Science, vol. 1, pp. 1288–1292, (1992).

*Primary Examiner*—Robert A. Wax
*Assistant Examiner*—Elizabeth Slobodyarisky
*Attorney, Agent, or Firm*—Steve T. Zelson, Esq.; Valeta A. Gregg, Esq.

[57] ABSTRACT

An enzyme exhibiting pectin methyl esterase activity, wherein the enzyme a) is derived from *Aspergillus aculeatus*; b) is encoded by Seq ID No:1; or c) has the amino acid sequence of Seq ID No:2 or a sequence which is at least 95% homologous thereto. An enzyme can be used for the modification of plant cell wall components.

11 Claims, 7 Drawing Sheets

ENZYME EXHIBITING PECTIN METHYLESTERASE ACTIVITY

This application is a 371 of PCT/DK94/00173, filed Apr. 28, 1994, which included the US as a designated state and claimed foreign priority benefits of DK 0487/93, filed Apr. 30, 1993 and DK 1217/93, filed Oct. 28, 1993.

FIELD OF INVENTION

The present invention relates to an enzyme with pectin methylesterase (PME) activity, a DNA construct encoding the enzyme, a method of producing the enzyme, an enzyme preparation containing the enzyme and various uses of the enzyme.

BACKGROUND OF THE INVENTION

Pectin polymers are important constituents of plant primary cell walls. They are mainly composed of chains of 1,4-linked α-D-galacturonic acid and methylated as well as acetylated derivatives thereof. The use of pectin-degrading enzymes is important in the food industry, primarily for fruit and vegetable processing Such as fruit juice production or wine making, where their ability to catalyse the degradation of the backbone of the pectin polymer is utilised.

An assortment of different pectin degrading enzymes is known to be present in various microorganisms such as *Aspergillus niger*. Of these, pectin methylesterase catalyses the removal of methanol from pectin, resulting in the formation of pectic acid (polygalacturonic acid). Pectate lyase cleaves glycosidic bonds in polygalacturonic acid by β-elimination, pectin lyase cleaves the glycosidic bonds of highly methylated pectins by β-elimination, and polygalacturonase hydrolyses the glycosidic linkages in the polygalacturonic acid chain.

The nucleotide and derived amino acid sequence of an *A. niger* pectin esterase cDNA sequence is disclosed by Khanh et al. (1990). EP 388 593 discloses the recombinant production of an *A. niger* pectin esterase in *A. awamori* or *A. niger*. Khanh et al. (1992) disclose the effect, on enzyme yield, of using various promoters in the expression of an *A. niger* pectin methyl esterase in *A. niger*.

Markovic and Jörnvall (1992) have analyzed disulfide bridges in a tomato pectin esterase and suggest the number and location of disulphide bridges in other known and distantly related pectin esterases from *A. niger, Erwinia chrysanthemi* and *Pseudomonas solanacearum*. Furthermore, various amino acid residues conserved between the various enzymes are identified and a possible location of the active site of the enzymes is suggested.

van Rijssel et al. (1993) disclose a protein complex isolated from *Clostridium thermosaccharolyticum* which has pectin methylesterase activity. WO 93/13212 discloses a tomato pectin esterase cDNA sequence.

WO 93/09683 discloses the use of a purified *A. niger* pectin esterase in the production of juice from fruits and vegetables.

SUMMARY OF THE INVENTION

It is an object of the present invention to prepare a single-component pectin methylesterase (PME).

Accordingly, the present invention relates to an enzyme exhibiting PME activity, which enzyme a) is immunologically reactive with an antibody raised against a purified PME derived from *Aspergillus aculeatus*, CBS 101.43, and/or b) is encoded by the coding part of the DNA sequence shown in SEQ ID No. 1 or a sequence homologous thereto encoding an enzyme exhibiting PME activity, and/or c) has the amino acid sequence shown in SEQ ID No. 2 or is at least 80% homologous with said sequence.

In the present context, the term "derived from" as used in connection with property a) is intended not only to indicate a PME produced by strain CBS 101.43, but also a PME encoded by a DNA sequence isolated from strain CBS 101.43 and produced in a host organism transformed with said DNA sequence.

In a further aspect, the invention relates to an enzyme exhibiting PME activity, which enzyme is encoded by a DNA sequence comprising the following partial sequence

```
TAAAGAGTCG ATCATACACT CATATCAATC GCAAAAATGG TTAAATCAGT           (SEQ ID NO: 3)
CTTGGCTTCC GCTCTCTTCG CCGCGTCCGC ACTGGCTGCC AGCCGTACCA
CGGCTCCCTC CGGCGCGATC GTCGTCGCCA AGTCTGGTGG TGACTATACC
ACTATTGGTG ATGCCATTGA TGCTCTGAGC ACCAGCACCA CCGACACCCA
AACCATTTTC ATCGAGGAG  GGTACCTAC  GATGAGCAGG TCTACCTGCC TGCTATGACC
GGCAAGGTCA TCATCTACGT CAAACCGAGA ACACCGACTC CTACG
``` or a sequence homologous thereto encoding a polypeptide with PME activity.

In the present context, the term "homologous" is intended to indicate a DNA which hybridizes to the same probe as the DNA coding for the PME enzyme under certain specified conditions (such as presoaking in 5xSSC and prehybridizing for 1 h at ~40° C. in a solution of 5xSSC, 5x Denhardt's solution, 50 mM sodium phosphate, pH 6.8, and 50 μg of denatured sonicated calf thymus DNA, followed by hybridization in the same solution supplemented with 50 μCi 32-P-dCTP labelled probe for 18 h at ~40° C. followed by washing three times in 2xSSC, 0.2% SDS at 40° C. for 30 minutes). More specifically, the term is intended to refer to a DNA sequence which is at least 80% homologous to the sequence shown in SEQ ID No. 1, such as at least 85% and preferably at least 90% or 95% homologous to this sequence. The term is intended to include modifications of the DNA sequences, such as nucleotide substitutions which do not give rise to another amino acid sequence of the PME but which correspond to the codon usage of the host organism into which the DNA construct is introduced or nucleotide substitutions which do give rise to a different amino acid sequence and therefore, possibly, a different protein structure which might give rise to a PME mutant with different properties than the native enzyme. Other examples of possible modifications are insertion of one or more nucleotides into the sequence, addition of one or more nucleotides at either end of the sequence, or deletion of one or more nucleotides at either end or within the sequence.

The term "homologous" as used in connection with a polypeptide or protein is intended to indicate the degree of identity with the amino acid sequence shown in SEQ ID No. 2, which may be determined by methods known in the art. Furthermore, the homologous polypeptide is preferably one which is encoded by an analogue (as defined above) of the DNA sequence shown in SEQ ID No. 1.

Furthermore, the invention relates to an enzyme exhibiting PME activity, which enzyme is encoded by a DNA sequence comprising at least one of the following partial sequences

| | | |
|---|---|---|
| (a) | TAAAGAGTCG ATCATACACT | (SEQ ID NO: 4) |
| (b) | CATATCAATC GCAAAAATGG | (SEQ ID NO: 5) |
| (c) | TTAAATCAGT CTTGGCTTCC | (SEQ ID NO: 6) |
| (d) | GCTCTCTTCG CCGCGTCCGC | (SEQ ID NO: 7) |
| (e) | ACTGGCTGCC AGCCGTACCA | (SEQ ID NO: 8) |
| (f) | CGGCTCCCTC CGGCGCGATC | (SEQ ID NO: 9) |
| (g) | GTCGTCGCCA AGTCTGGTGG | (SEQ ID NO: 10) |
| (h) | TGACTATACC ACTATTGGTG | (SEQ ID NO: 11) |
| (i) | ATGCCATTGA TGCTCTGAGC | (SEQ ID NO: 12) |
| (j) | ACCAGCACCA CCGACACCCA | (SEQ ID NO: 13) |
| (k) | AACCATTTTC ATCGAGGAG | (SEQ ID NO: 14) |
| (l) | GGTACCTAC GATGAGCAGG | (SEQ ID NO: 15) |
| (m) | TCTACCTGCC TGCTATGACC | (SEQ ID NO: 16) |
| (n) | GGCAAGGTCA TCATCTACGT | (SEQ ID NO: 17) |
| (o) | CAAACCGAGA ACACCGACTC CTACG | (SEQ ID NO: 18) |

In a further aspect the invention relates to a DNA construct comprising a DNA sequence encoding an enzyme exhibiting pectin methyl esterase activity, which DNA sequence comprises the coding part of the DNA sequence shown in SEQ ID No. 1 or any of the partial DNA sequence shown above, or is an analogue of said sequence, which i) hybridizes with an oligonucleotide probe prepared on the basis of any of the partial DNA sequences shown above, of the DNA sequence shown in SEQ ID No. 1, or of the amino acid sequence shown in SEQ ID No. 2, ii) encodes an enzyme comprising an amino acid sequence being at least 80% homologous with the amino acid sequence shown in SEQ ID No. 2 such as at least 85%, 90% or 95% homologous with said sequence, and/or iii) encodes an enzyme which is immunologically cross-reactive with the polypeptide comprising the amino acid sequence shown in SEQ ID No. 2.

DETAILED DESCRIPTION OF THE INVENTION

Figure 1:
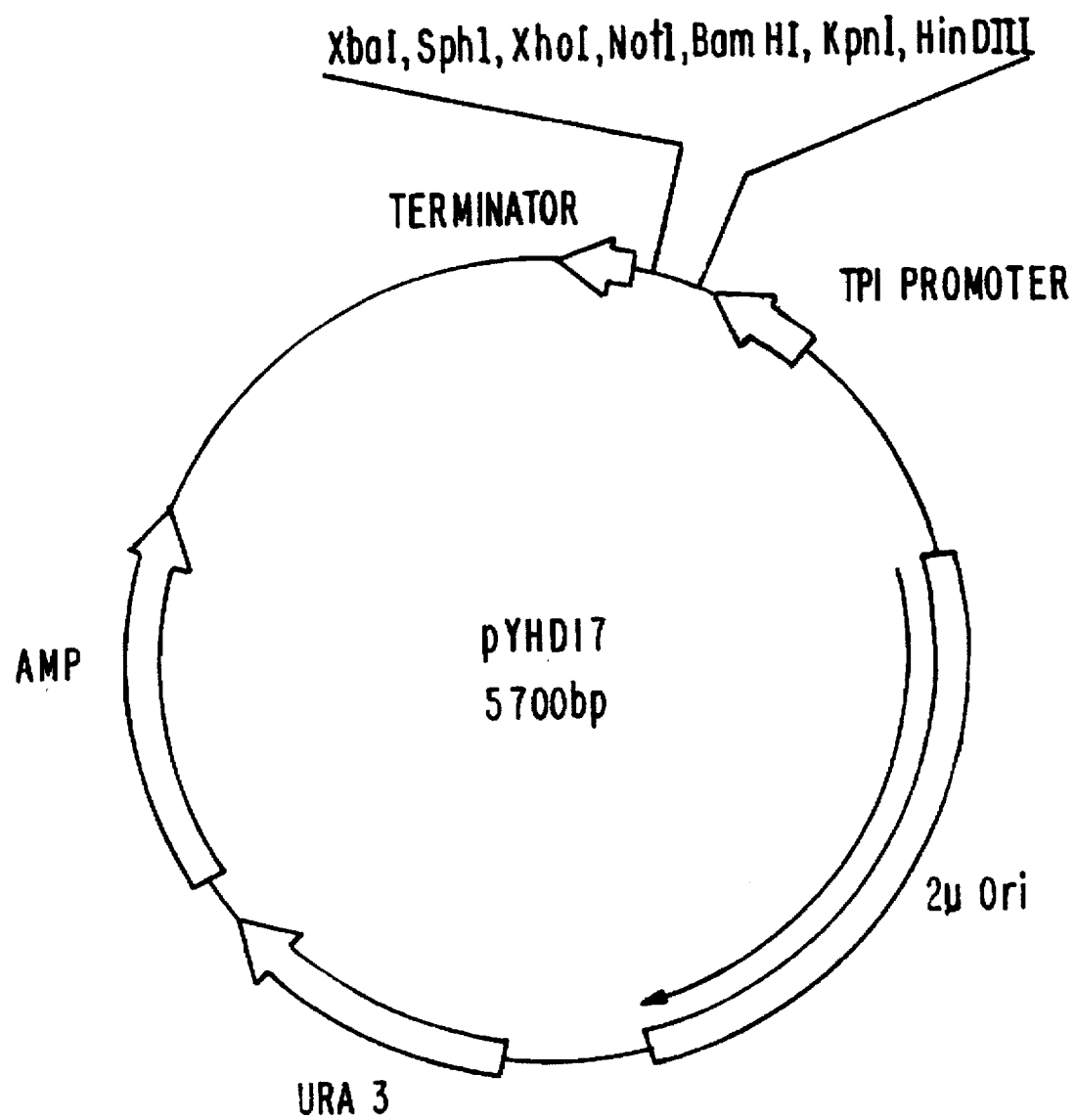

The enzyme of the invention may be isolated by a general method involving cloning, in suitable vectors, a DNA library from *Aspergillus aculeatus*, transforming suitable yeast host cells with said vectors, culturing the host cells under suitable conditions to express any enzyme of interest encoded by a clone in the DNA library, and screening for positive clones by determining any PME activity of the enzyme produced by such clones.

A more detailed description of this screening method is given in Example 1 below.

The DNA sequence coding for the enzyme may for instance be isolated by screening a cDNA library of *Aspergillus aculeatus*, e.g strain CBS 101.43, publicly available from the Centraalbureau voor Schimmelcultures, Delft, NL, and selecting for clones expressing the appropriate enzyme activity (i.e. PME activity as defined by the ability of the enzyme to hydrolyse methylester bonds in pectin).

The appropriate DNA sequence may then be isolated from the clone by standard procedures, e.g. as described in Example 1. It is expected that DNA encoding a homologous enzyme may be isolated by similarly screening a cDNA library of another microorganism, in particular a fungus, such as a strain of an Aspergillus sp., in particular a strain of *A. aculeatus*, *A. oryzae* or *A. niger*, a strain of a Trichoderma sp., in particular a strain of *T. harzianum* or *T. reesie*, a strain of a Fusarium sp., in particular a strain of *F. oxysporum*, a strain of a Humicola sp. or a strain of a Geotricum sp.

Alternatively, the DNA coding for a PME of the invention may, in accordance with well-known procedures, conveniently be isolated from DNA from any of the above mentioned organisms by use of synthetic oligonucleotide probes, prepared on the basis of a DNA sequence disclosed herein. For instance, a suitable oligonucleotide probe may be prepared on the basis of any of the partial nucleotide sequences (a)–(o) listed above.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the PME should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the PME, the promoter and the terminator, respectively, and to insert them into suitable vectors are well known to persons skilled in the art (cf., for instance, Sambrook et al., *Molecular Cloning. A Laboratory Manual*, Cold Spring Harbor, N.Y., 1989).

The host cell which is transformed with the DNA sequence encoding the enzyme of the invention is preferably a eukaryotic cell, in particular a fungal cell such as a yeast or filamentous fungal cell. In particular, the cell may belong to a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of *Aspergillus oryzae* as a host microorganism is described in EP 238 023 (of Novo Industri A/S), the contents of which are hereby incorporated by reference. The host cell may also be a yeast cell, e.g. a strain of Saccharomyces, in particular *Saccharomyces cerevisiae*.

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed PME may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The thus purified PME may be employed for immunization of animals for the production of antibodies. More specifically, antiserum against the PME of the invention may be raised by immunizing rabbits (or other rodents) according to the procedure described by N. Axelsen et al. in: *A Manual of Quantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation ($(NH_4)_2SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2,).

In a still further aspect, the present invention relates to an enzyme preparation useful for the degradation of plant cell wall components, said preparation being enriched in an enzyme exhibiting PME activity as described above.

The enzyme preparation having been enriched with an enzyme of the invention may e.g. be an enzyme preparation comprising multiple enzymatic activities, in particular an enzyme preparation comprising multiple plant cell wall degrading enzymes such as Pectinex® or Pectinex Ultra SP® (Novo Nordisk A/S). In the present context, the term "enriched" is intended to indicate that the PME activity of the enzyme preparation has been increased, e.g. with an enrichment factor of at least 1.1, conveniently due to addition of an enzyme of the invention prepared by the method described above.

Alternatively, the enzyme preparation enriched in an enzyme exhibiting PME activity may be one which comprises an enzyme of the invention as the major enzymatic component, e.g. a mono-component enzyme preparation.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

Based on its great activity on pectin containing material, typically of plant cell wall origin, a preferred use of the enzyme preparation according to the invention is as an agent for degradation or modification of plant cell wall material or other pectin containing material.

The enzyme of the invention may advantageously be used together with other enzymes, especially other pectin degrading enzymes when the enzyme is to be used in the processing of fruits, vegetables and other plant materials. Accordingly, the enzyme preparation of the invention may in addition to the PME comprise one or more other plant cell wall degrading enzymes such as a polygalacturonase, pectin lyase, pectate lyase, arabinanase, xylanase, glucanase, galactanase, mannanase, rhamnogalacturonase, rhamnogalacturonan acetyl esterase or pectin acetylesterase. The preparation may further contain one or more enzymes exhibiting exo-activity on the same substrates as the above-mentioned endo-enzymes. In particular, the enzyme may be used in combination with polygalacturonase, pectate lyase or pectin lyase in pectin degradation.

Examples are given below of preferred uses of an enzyme preparation of the invention comprising an enzyme exhibiting pectin methyl esterase activity, optionally in combination with one or more other enzymes. The dosage of the enzyme preparation of the invention and other conditions under which the preparation is used may be determined on the basis of methods known in the art.

The enzyme preparation may advantageously be used for the treatment of pectin containing plant material, e.g. of vegetable or fruit origin, such as material obtained from soy beans, sugar beets or apples, so as to reduce the viscosity and thus improve the processing or appearance of the plant material in question. The viscosity reduction may be obtained by treating the pectin-containing plant material with an enzyme preparation of the invention under suitable conditions for full or partial degradation of the pectin-containing material.

The enzyme preparation may be used for de-pectinization and viscosity reduction in vegetable or fruit juice, especially in apple or pear juice.

The enzyme preparation may be used in the treatment of mash from fruits and vegetables, for instance in the mash treatment of apples and pears for juice production, and in the mash treatment of grapes for wine production.

The enzyme preparation may be used in the production of citrus juice, e.g. for partial or complete degradation of the pulp present in the juice after pressing.

For the above uses it is preferred that the enzyme preparation in addition to PME comprises a polygalacturonase containing enzyme preparation.

By use of an enzyme preparation of the invention it is possible to regulate the consistency and appearance of processed fruit or vegetables. Thus, the consistency and appearance have been found to be a product of the actual combination of enzymes used for the processing, i.e. the nature of the enzymes (especially pectin degrading enzyme(s)) with which the pectin methyl esterase of the invention is combined.

Examples of products with specific properties which may be produced by use of an enzyme preparation of the invention include clear juice from apples, pears or berries, cloud stable juice from apples, pears, berries, citrus, or tomatoes, and purees from carrots and tomatoes.

From the foregoing disclosure it will be apparent that the PME of the invention may be produced as a single component essentially free from other enzyme activities such as polygalacturonase and/or pectin lyase activity normally found to be present in commercially available pectinesterase containing pectinolytic preparations.

On this basis the use of the PME of the invention is especially advantageous for purposes in which the action of such other enzyme activities are undesirable.

Examples of such purposes include the use of the pectin methylesterase for full or partial demethylation of pectin in processed or non-processed fruits and vegetables.

The partial demethylation is, e.g., important when an improved firmness of fruits or vegetables is desirable. Thus, firmness is often reduced during processing (e.g. canning and pasteurization). By use of a controlled amount of a PME of the invention a partial demethylation of pectin present in the surface of fruits and vegetables may be obtained and the resulting partially demethylated pectin may crosslink with, e.g., divalent ions such as calcium, whereby a more firm surface of the fruits or vegetables may be formed. Accordingly, the PME of the invention may be used for improving the firmness of, e.g., beans, peas and sliced fruits such as pears and apples.

Another example of the purposes is demethylation of pectin, e.g. from citrus, apple, sunflower and/or sugar beet. The PME can be used to produce low methylated pectin (defined as pectins where under 50% of the galacturonic acids are methylated) from high methylated pectin (defined as pectin where over 50% of the galacturonic acids are methylated). Conventionally, such demethylation has been carried out by alkaline or acid demethylation which has the drawback, among others, that the demethylation needs to be carefully controlled in order to avoid depolymerization of the pectin backbone and thereby a severe reduction of the functional properties of the demethylated pectin.

By use of a PME of the invention the above described depolymerization is avoided and the demethylation is performed under milder conditions and within a reasonable temperature (15°–50° C.) and time level (10 min.–2 hours).

Furthermore, the pectin esterase can be used to obtain an in situ viscosity increase or gel formation in various vegetable or fruit based products, when added together (simultaneously or non-simultaneously) with medium or high methylated pectin. The resulting low methylated pectin will, in the presence of, e.g., divalent ions, form a more viscous liquid or a gel. Alternatively, the natural content of pectin may be demethylated by use of the enzyme, whereby the addition of pectin may be reduced or even avoided.

By use of this process it is possible to avoid or reduce the amount of pectin to be added. This is advantageous in that the addition of, e.g., low-methylated pectin may give rise to gelation during mixing which again may result in an incomplete mixing being obtained. Furthermore, low-methylated pectin may be difficult to dissolve in water.

The use of PME for viscosity increase or gel formation eliminates or reduces the addition of other stabilizing or gelling agents in, e.g., jam and ketchup. Thus, the demethoxylation of the natural content of pectin, which is induced by the enzyme, may, upon reaction with the natural content of metal ions, be sufficient for a satisfactory viscosity increase or gelformation to take place.

For the viscosity increase the amount of pectin methyl esterase to be added is typically in the range 0.1–100 PMEU per g of pectin, particularly 1–10 PMEU per g. The PME activity (PMEU) is defined in the Materials and Methods section below.

The PME of the invention can alone or together with other enzymes be used to improve the digestibility of pectin containing animal feed, e.g. feed prepared from soya beans, sugar beets or rape seeds. For this purpose, an enzyme preparation of the invention is added to the feed.

The pectin esterase activity can together with other enzymes be used to produce monogalacturonic acid or galacturonic acid containing oligosaccharides from pectin-containing material such as sugar beet pulp in accordance with well-known methods. Monogalacturonic acid may be used for production of galactaric acid or for production of fatty acid and fatty alcohol esters and/or ethers of galacturonic acid. Galacturonic containing oligosaccharides may be used as additives for human food or animal feed.

Furthermore, the PME can in combination with other enzymes be used for the removal of pectic substances from plant fibres, which removal is essential, e.g. in the production of textile fibres or other cellulosic materials. For this purpose plant fibre material is treated with a suitable amount of the PME of the invention under suitable conditions for obtaining full or partial degradation of pectic substances associated with the plant fibre material.

The invention is further described in the accompanying drawing in which

Figure 2:
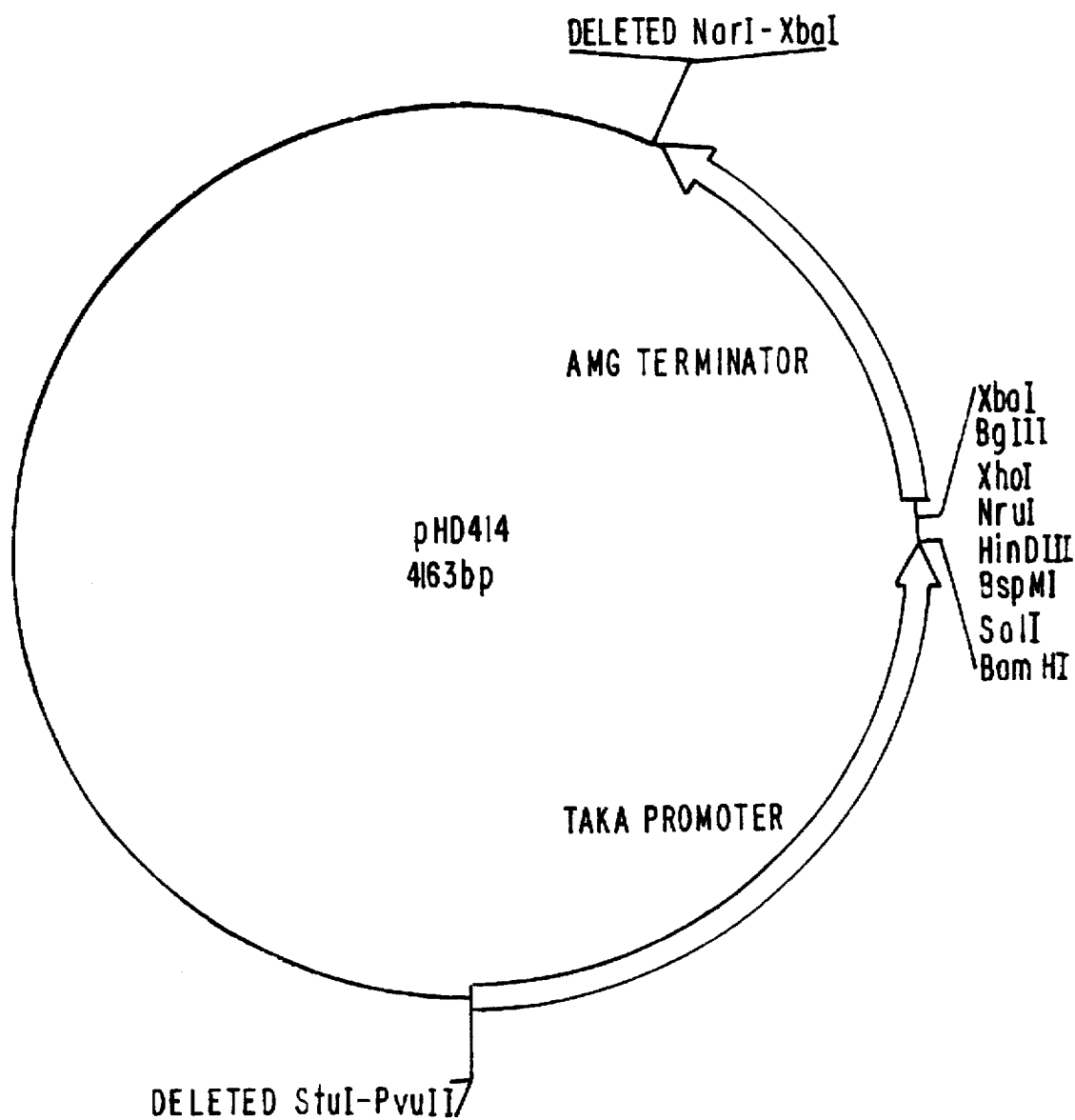
Figure 3:
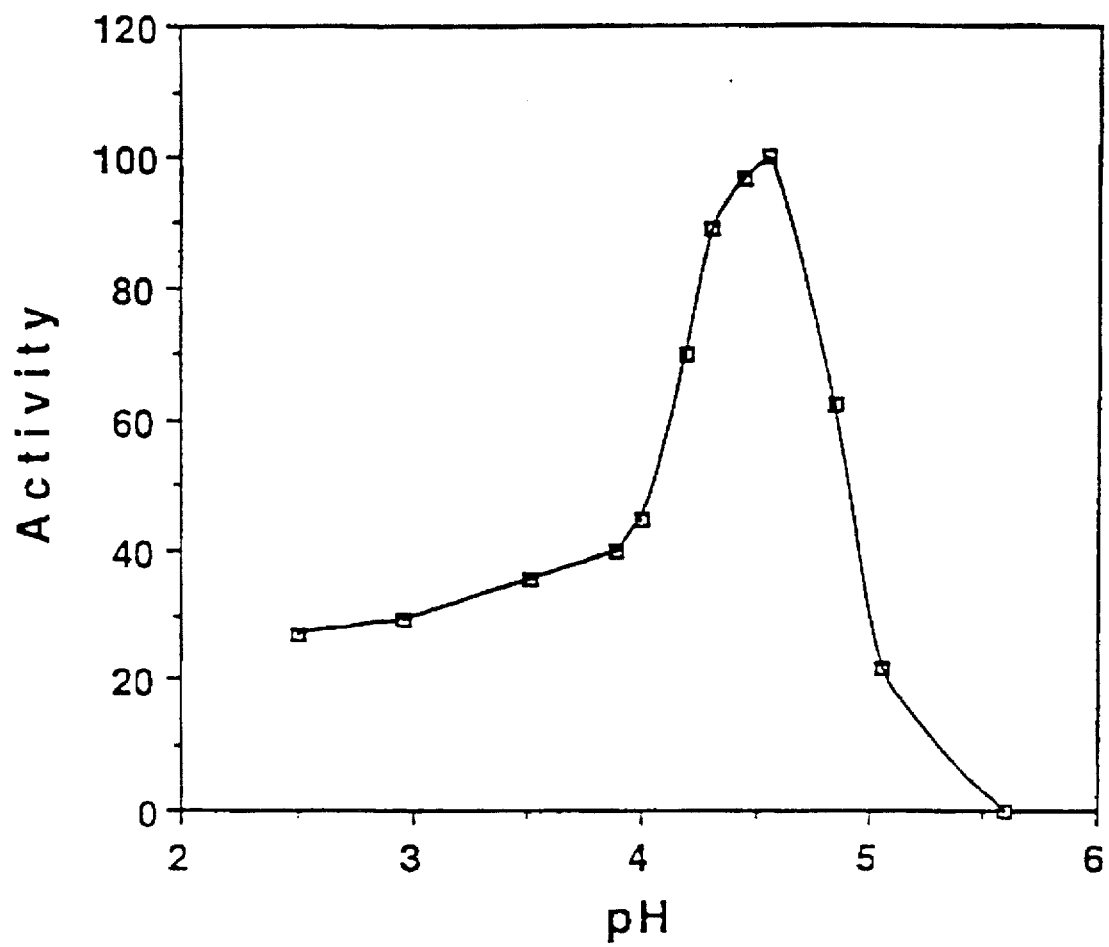
Figure 4:
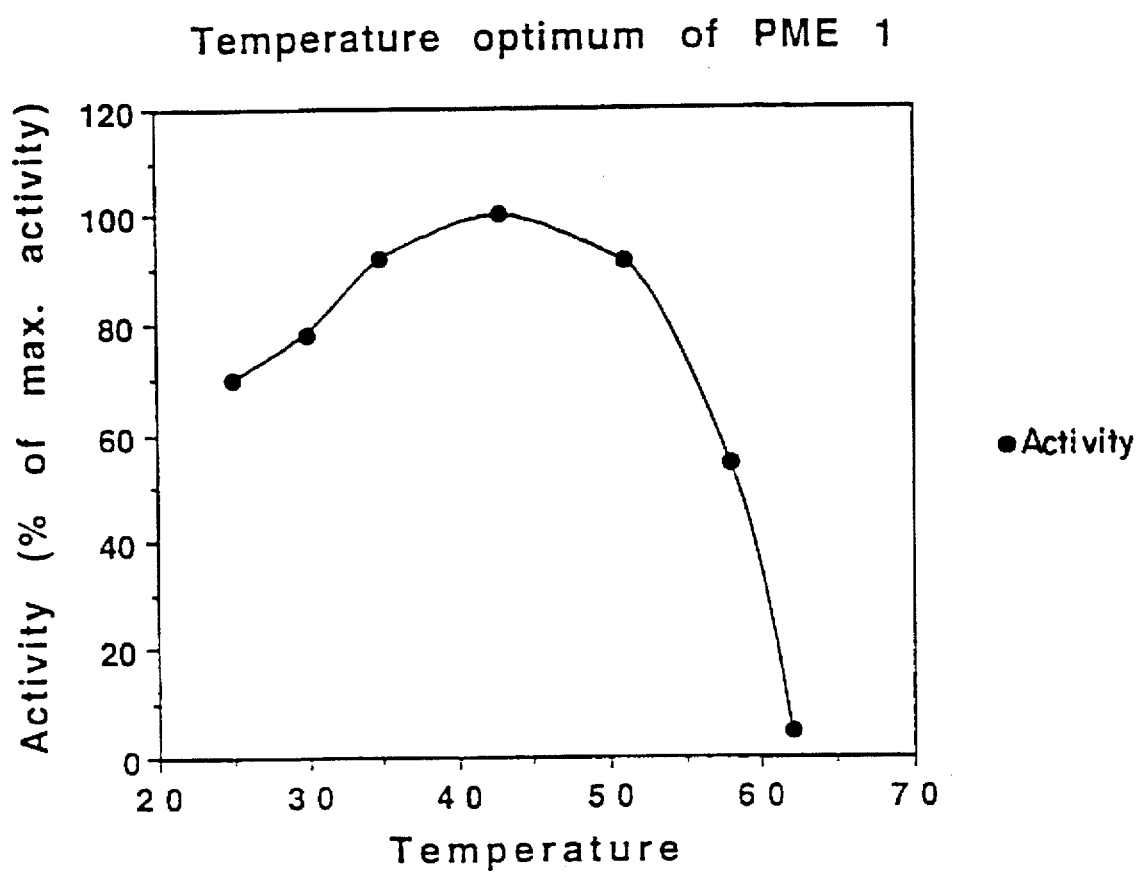
Figure 5:
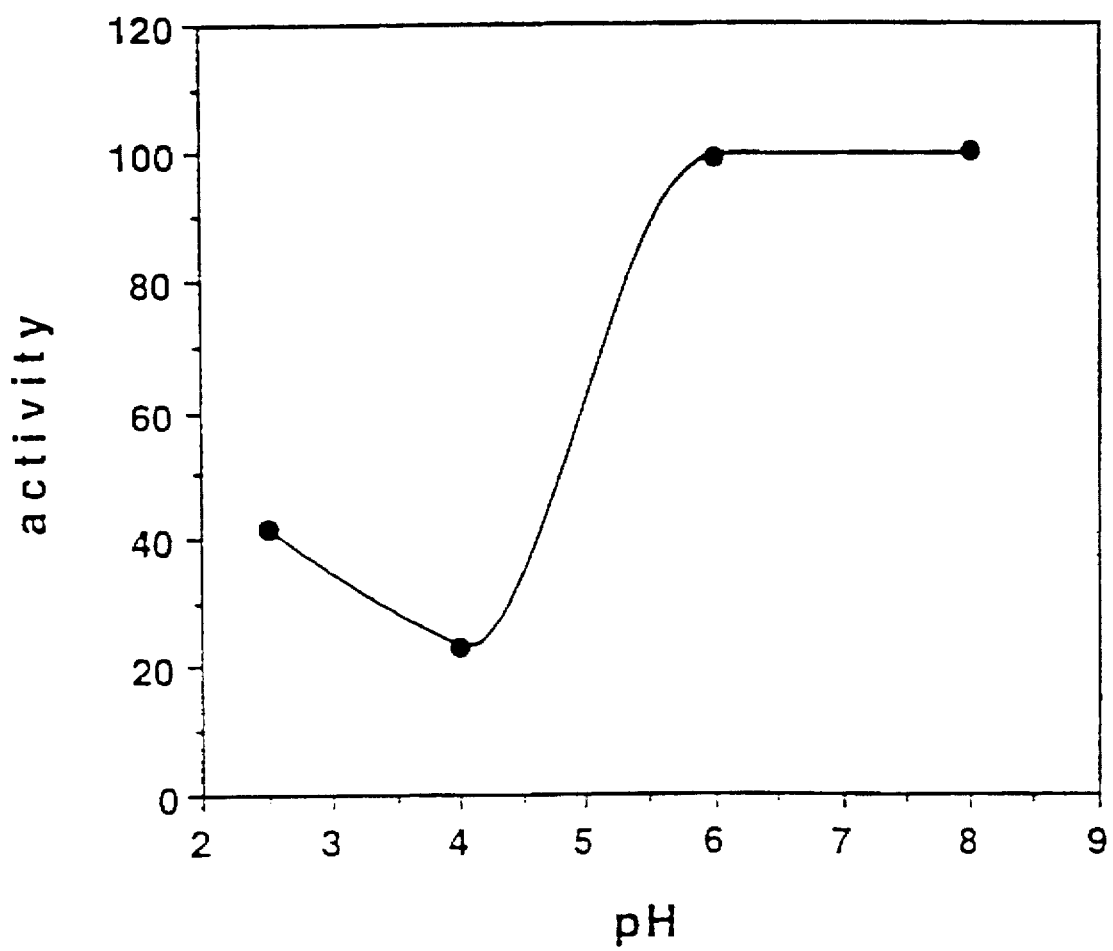
Figure 6:
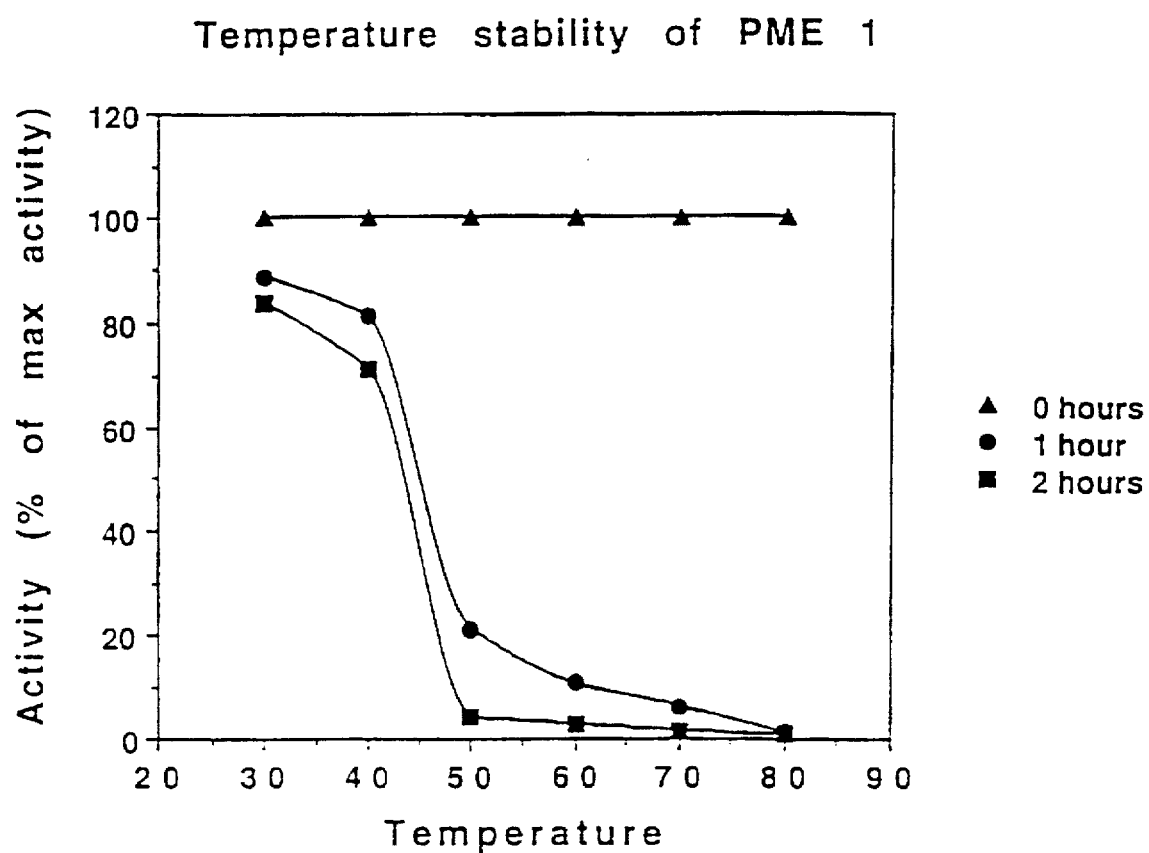
Figure 7:
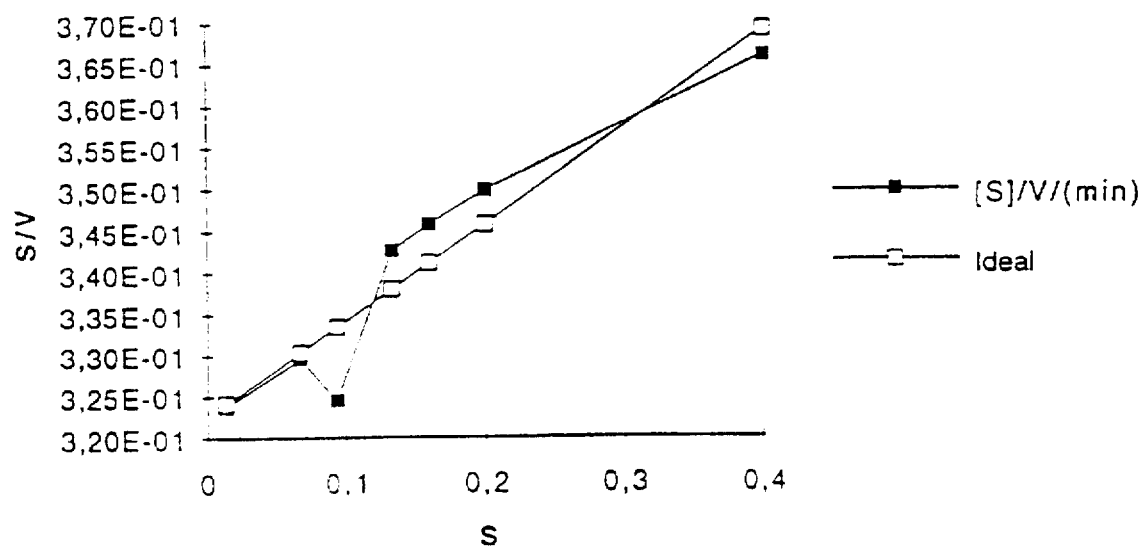

FIG. 1 is a restriction map of plasmid pYHD17,
FIG. 2 a restriction map of plasmid pHD 414,
FIG. 3 a pH optimum curve,
FIG. 4 a temperature optimum curve,
FIG. 5 a pH stability curve,
FIG. 6 a temperature stability curve, and
FIG. 7 the [S]/V versus [S] curve used for Km and spec. act. determination.

The invention is described in further detail in the following examples which are not in any way intended to limit the scope of the invention as claimed.

EXAMPLES

Materials and Methods

Donor organism: mRNA was isolated from *Aspergillus aculeatus*, CBS 101.43, grown in a soy-containing fermentation medium with agitation to ensure sufficient aeration. Mycelia were harvested after 3–5 days' growth, immediately frozen in liquid nitrogen and stored at –80° C.

Yeast strains: The *Saccharomyces cerevisiae* strain used was yNG231 (MAT alpha, leu2, ura3-52, his4-539, pep4-delta 1, cir+) or JG169 (MATα; ura 3-52; leu 2-3, 112; his 3-D200; pep 4-113; prc1::HIS3; prb1:: LEU2; cir+).

Construction of an expression plasmid: The commercially available plasmid pYES II (Invitrogen) was cut with SpeI, filled in with Klenow DNA polymerase+dNTP and cut with ClaI. The DNA was size fractionated on an agarose gel, and a fragment of about 2000 bp was purified by electroelution. The same plasmid was cut with ClaI/PvuII, and a fragment of about 3400 bp was purified by electroelution. The two fragments were ligated to a blunt-ended SphI/EcoRI fragment containing the yeast TPI promoter. This fragment was isolated from a plasmid in which the TPI promoter from *S. cerevisiae* (cf. T. Albers and G. Kawasaki, *J. Mol. Appl. Genet.* 1, 1982, pp. 419–434) was slightly modified: an internal SphI site was removed by deleting the four bp constituting the core of this site. Furthermore, redundant sequences upstream of the promoter were removed by Bal1 exonuclease treatment followed by addition of a SphI linker. Finally, an EcoRI linker was added at position—10. After these modifications, the promoter is included in a SphI-EcoRI fragment. Its effeciency compared to the original promoter appears to be unaffected by the modifications. The resulting plasmid pYHD17 is shown in FIG. 1.

Preparation of RNase-free glassware, tips and solutions: All glassware used in RNA isolations was baked at +220° C. for at least 12 h. Eppendorf tubes, pipet tips and plastic columns were treated in 0.1% diethylpyrocarbonate (DEPC) in EtOH for 12 h, and autoclaved. All buffers and water (except Tris-containing buffers) were treated with 0.1% DEPC for 12 h at 37° C., and autoclaved.

Extraction of total RNA: The total RNA was prepared by extraction with guanidinium thiocyanate followed by ultra-centrifugation through a 5.7M CsCl cushion (Chirgwin et al., 1979) using the following modifications. The frozen mycelia were ground in liquid $N_2$ to fine powder with a mortar and a pestle, followed by grinding in a precooled coffee mill, and immediately suspended in 5 vols of RNA extraction buffer (4M GuSCN, 0.5% Na-laurylsarcosine, 25 mM Na-citrate, pH 7.0, 0.1M β-mercaptoethanol). The mixture was stirred for 30 min. at RT° and centrifuged (30 min., 5000 rpm, RT°, Heraeus Megafuge 1.0 R) to pellet the cell debris. The supernatant was collected, carefully layered onto a 5.7M CsCl cushion (5.7M CsCl, 0.1M EDTA, pH 7.5, 0.1% DEPC; autoclaved prior to use) using 26.5 ml supernatant per 12.0 ml CsCl cushion, and centrifuged to obtain the total RNA (Beckman, S. W. 28 rotor, 25000 rpm, RT°, 24h). After centrifugation the supernatant was carefully removed and the bottom of the tube containing the RNA pellet was cut off and rinsed with 70% EtOH. The total RNA pellet was transferred into an Eppendorf tube, suspended in 500 µl TE, pH 7.6 (if difficult, heat occasionally for 5 min at 65° C.), phenol extracted and precipitated with ethanol for 12 h at −20° C. (2.5 vols EtOH, 0.1 vol 3M NaAc, pH 5.2). The RNA was collected by centrifugation, washed in 70% EtOH, and resuspended in a minimum volume of DEPC-DIW. The RNA concentration was determined by measuring $OD_{260/280}$.

Isolation of poly(A)⁺RNA: The poly(A)+RNAs were isolated by oligo (dT) -cellulose affinity chromatography (Aviv & Leder, 1972). Typically, 0.2 g of oligo(dT) cellulose (Boehringer Mannheim) was preswollen in 10 ml of 1×column loading buffer (20 mM Tris-Cl, pH 7.6, 0.5M NaCl, 1 mM EDTA, 0.1% SDS), loaded onto a DEPC-treated, plugged plastic column (Poly Prep Chromatography Column, Bio Rad), and equilibrated with 20 ml 1×loading buffer. The total RNA was heated at 65 C. for 8 min., quenched on ice for 5 min, and after addition of 1 vol 2×column loading buffer to the RNA sample loaded onto the column. The eluate was collected and reloaded 2–3 times by heating the sample as above and quenching on ice prior to each loading. The oligo(dT) column was washed with 10 vols of 1×loading buffer, then with 3 vols of medium salt buffer (20 mM Tris-Cl, pH 7.6, 0.1M NaCl, 1 mM EDTA, 0.1% SDS), followed by elution of the poly(A)⁺RNA with 3 vols of elution buffer (10 mM Tris-Cl, pH 7.6, 1 mM EDTA, 0.05% SDS) preheated to +65° C., by collecting 500 µl fractions. The $OD_{260}$ was read for each collected fraction, and the mRNA containing fractions were pooled and ethanol precipitated at −20° C. for 12 h. The poly(A)⁺RNA was collected by centrifugation, resuspended in DEPC-DIW and stored in 5–10 µg aliquots at −80° C.

Northern blot analysis: The poly(A)⁺ RNAs (5 µg/sample) from various mycelia were electrophoresed in 1.2 agarose-2.2M formaldehyde gels (Sambrook et al., 1989) and blotted to nylon membranes (Hybond-N, Amersham) with 10×SSC (Sambrook et al., 198.9) as transfer buffer. Three random-primed (Feinberg & Vogelstein, 1983) $^{32}$P-labeled cDNA probes were used in individual hybridizations: 1) a 1.3 kb Not I-Spe I fragment for polygalacturonase I from A. aculeatus (described in Danish Patent Application DK 1545/92), 2) a 1.3 kb Not I-Spe I fragment encoding endoglucanase I from A. aculeatus (described in DK 0419/92) and 3) a 1.2 kb Eag I fragment coding for galactanase I from A. aculeatus (described in WO 92/13945). Northern hybridizations were carried out in 5×SSC (Sambrook et al., 1989), 5×Denhardt's solution (Sambrook et al., 1989), 0.5% SDS (w/v) and 100 µg/ml denatured salmon sperm DNA with a probe concentration of ca. 2 ng/ml for 16 h at 65° C. followed by washes in 5×SSC at 65° C. (2×15 min), 2×SSC, 0.5% SDS (1×30 min), 0.2×SSC, 0.5% SDS (1×30 min), and 5×SSC (2× 15 min). After autoradiography at −80° C. for 12 h, the probe #1 was removed from the filter according to the manufacturer's instructions and rehybridized with probe #2, and eventually with probe #3. The RNA ladder from Bethesda Research Laboratories was used as a size marker.

cDNA synthesis

First strand synthesis: Double-stranded cDNA was synthesized from 5 µg of A. aculeatus poly(A)⁺ RNA by the RNase H method (Gubler & Hoffman 1983, Sambrook et al., 1989) using the hair-pin modification. The poly(A)⁺RNA (5 µg in 5 µl of DEPC-treated water) was heated at 70° C. for 8 min., quenched on ice, and combined in a final volume of 50 µl with reverse transcriptase buffer (50 mM Tris-Cl, pH 8.3, 75 mM KCl, 3 mM MgC2, 10 mM DTT, Bethesda Research Laboratories) containing 1 mM each dNTP (Pharmacia), 40 units of human placental ribonuclease inhibitor (RNasin, Promega), 10 µg of oligo(dT)$_{12-18}$ primer (Pharmacia) and 1000 units of SuperScript II RNase H-reverse transcriptase (Bethesda Research Laboratories). First-strand cDNA was synthesized by incubating the reaction mixture at 45° C. for 1 h.

Second strand synthesis: After synthesis 30 µl of 10 mM Tris-Cl, pH 7.5, 1 mM EDTA was added, and the mRNA: cDNA hybrids were ethanol precipitated for 12 h at −20° C. by addition of 40 µg glycogen carrier (Boehringer Mannheim) 0.2 vols 10M NH$_4$Ac and 2.5 vols 96% EtOH. The hybrids were recovered by centrifugation, washed in 70% EtOH, air dried and resuspended in 250 µl of second strand buffer (20mM Tris-Cl, pH 7.4, 90 mM KCl, 4.6 mM MgCl2, 10 mM (NH$_4$)$_2$SO$_4$, 16 µM βNAD⁺) containing 100 µM each dNTP, 44 units of E. coli DNA polymerase I (Amersham), 6.25 units of RNase H (Bethesda Research Laboratories) and 10.5 units of E. coli DNA ligase (New England Biolabs). Second strand cDNA synthesis was performed by incubating the reaction tube at 16° C. for 3 h, and the reaction was stopped by addition of EDTA to 20 mM final concentration followed by phenol extraction.

Mung bean nuclease treatment: The double-stranded (ds) cDNA was ethanol precipitated at −20° C. for 12 h by addition of 2 vols of 96% EtOH, 0.1 vol 3M NaAc, pH 5.2, recovered by centrifugation, washed in 70% EtOH, dried (SpeedVac), and resuspended in 30 µl of Mung bean nuclease buffer (30 mM NaAc, pH 4.6, 300 mM NaCl, 1 mM ZnSO4, 0.35 mM DTT, 2% glycerol) containing 36 units of Mung bean nuclease (Bethesda Research Laboratories). The single-stranded hair-pin DNA was clipped by incubating the reaction at 30° C. for 30 min, followed by addition of 70 µl 10 mM Tris-Cl, pH 7.5, 1 mM EDTA, phenol extraction, and ethanol precipitation with 2 vols of 96% EtOH and 0.1 vol 3M NaAc, pH 5.2 at −20° C. for 12 h.

Blunt-ending with T4 DNA polymerase: The ds cDNA was blunt-ended with T4 DNA polymerase in 50 µl of T4 DNA polymerase buffer (20 mM Tris-acetate, pH 7.9, 10 mM MgAc, 50 mM KAc, 1 mM DTT) containing 0.5 mM each dNTP and 7.5 units of T4 DNA polymerase (Invitrogen) by incubating the reaction mixture at +37° C. for 15 min. The reaction was stopped by addition of EDTA to 20 mM final concentration, followed by phenol extraction and ethanol precipitation.

Adaptor ligation and size selection: After the fill-in reaction the cDNA was ligated to non-palindromic BstX I adaptors (1 µg/µl, Invitrogen) in 30 µl of ligation buffer (50 mM Tris-Cl, pH 7.8, 10mM MgCl2, 10mM DTT, 1 mM ATP, 25 µg/ml bovine serum albumin) containing 600 pmol BstX I adaptors and 5 units of T4 ligase (Invitrogen) by incubating the reaction mix at +16° C. for 12 h. The reaction was stopped by heating at +70° C. for 5 min, and the adapted cDNA was size-fractionated by agarose gel electrophoresis (0.8% HSB-agarose, FMC) to separate unligated adaptors and small cDNAs. The cDNA was size-selected with a cut-off at 0.7 kb, and the cDNA was electroeluted from the agarose gel in 10 mM Tris-Cl, pH 7.5, 1 mM EDTA for 1 h at 100 volts, phenol extracted and ethanol precipitated at −20° C. for 12 h as above.

Construction of cDNA libraries: The adapted, ds cDNA was recovered by centrifugation, washed in 70% EtOH and resuspended in 25 ml DIW. Prior to large-scale library ligation, four test ligations were carried out in 10 μl of ligation buffer (same as above) each containing 1 μl ds cDNA (reaction tubes #1–#3), 2 units of T4 ligase (Invitrogen) and 50 ng (tube #1), 100 ng (tube #2) and 200 ng (tubes #3 and #4) Bst XI cleaved yeast expression vector either pYES 2.0 vector Invitrogen or yHD13). The ligation reactions were performed by incubation at +16° C. for 12 h, heated at 70° C. for 5 min, and 1 μl of each ligation electroporated (200 Ω, 2.5 kV, 25 μF) to 40 μl competent E. coli 1061 cells (OD600=0.9 in 1 liter LB-broth, washed twice in cold DIW, once in 20 ml of 10% glycerol, resuspended in 2 ml 10% glycerol). After addition of 1 ml SOC to each transformation mix, the cells were grown at +37° C. for 1 h, 50 μl plated on LB+ampicillin plates (100 μg/ml) and grown at +37° C. for 12 h.

Using the optimal conditions a large-scale ligation was set up in 40 μl of ligation buffer containing 9 units of T4 ligase, and the reaction was incubated at +16° C. for 12 h. The ligation reaction was stopped by heating at 70° C. for 5 min, ethanol precipitated at −20° C. for 12 h, recovered by centrifugation and resuspended in 10 μl DIW. One μl aliquots were transformed into electrocompetent E. coli 1061 cells using the same electroporation conditions as above, and the transformed cells were titered and the library plated on LB+ampicillin plates with 5000–7000 c.f.u./plate. To each plate was added 3 ml of medium. The bacteria were scraped off, 1 ml glycerol was added and stored at −80° C. as pools. The remaining 2 ml were used for DNA isolation. If the amount of DNA was insufficient to give the required number of yeast transformants, large scale DNA was prepared from 500 ml medium (TB) inoculated with 50 μl of −80° C. bacterial stock propagated overnight.

Construction of yeast libraries: To ensure that all the bacterial clones were tested in yeast, a number of yeast transformants 5 times larger than the number of bacterial clones in the original pools was set as the limit.

One μl aliquots of purified plasmid DNA (100 ng/μl) from individual pools were electroporated (200 Ω, 1.5 kV, 25 μF) into 40 μl competent S. cerevisiae JG 169 cells (0D600=1.5 in 500 ml YPD, washed twice in cold DIW, once in cold 1M sorbitol, resuspended in 0.5 ml 1M sorbitol, Becker & Guarante, 1991). After addition of 1 ml 1M cold sorbitol, 80 μl aliquots were plated on SC+glucose—uracil to give 250–400 c.f.u./plate and incubated at 30° C. for 3–5 days.

Construction of an Aspergillus expression vector: the vector pHD414 is a derivative of the plasmid p775 (described in EP 238 023). In contrast to this plasmid, pHD 414 has a string of unique restriction sites between the promoter and the terminator. The plasmid was constructed by removal of an approximately 200 bp long fragment (containing undesirable RE sites) at the 3'end of the terminator, and subsequent removal of an approximately 250 bp long fragment at the 5'end of the promoter, also containing undesirable sites. The 200 bp region has removed by cleavage with NarI (positioned in the pUC vector) and XbaI (just 3' to the terminator), subsequent filling in the generated ends with Klenow DNA polymerass +dNTP, purification of the vector fragment on gel and religation of the vector fragment. This plasmid was called pHD413. pHD413 was cut with StuI (positioned in the 5'end of the promoter) and PvuII (in the pUC vector), fractionated on gel and religated. The plasmid pHD 414 is shown in FIG. 2.

Media:
YPD: 10 g yeast extract, 20 g peptone, H₂O to 810 ml. Autoclaved, 90 ml 20% glucose (sterile filtered) added.

10×Basal salt: 66.8 g yeast nitrogen base, 100 g succinic acid, 60 g NaOH, H₂O ad 1000 ml, sterile filtered.

SC-URA: 90 ml 10×Basal salt, 22.5 ml 20% casamino acids, 9 ml 1% tryptophan, H₂O ad 806 ml, autoclaved, 3.6 ml 5% threonine and 90 ml 20% glucose or 20% galactose added.

SC-H broth: 7.5 g/l yeast nitrogen base without amino acids, 11.3 g/l succinic acid, 6.8 g/l NaOH, 5.6 g/l casamino acids without vitamins, 0.1 g/l tryptophan. Autoclaved for 20 min. at 121° C. After autoclaving, 10 ml of a 30% galactose solution, 5 ml of a 30% glucose solution and 0.4 ml of a 5% threonine solution were added per 100 ml medium.

SC-H agar: 7.5 g/l yeast nitrogen base without amino acids, 11.3 g/l succinic acid, 6.8 g/l NaOH, 5.6 g/l casamino acids without vitamins, 0.1 g/l tryptophan, and 20 g/l agar (Bacto). Autoclaved for 20 min. at 121° C. After autoclaving, 55 ml of a 22% galactose solution and 1.8 ml of a 5% threonine solution were added per 450 ml agar.

YNB-1 agar: 3.3 g/l KH₂PO₄, 16.7 g/l agar, pH adjusted to 7. Autoclaved for 20 min. at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth: Composition as YNB-1 agar, but without the agar.

FG-4-Agar: 35 g/L agar, 30 g/L Soy bean meal, 15 g/L maltodextrin (Glucidex 6), 5 g/L Bacto pepton, pH 7. Autoclaved 40 min at 121° C.

FG-4 medium: 30 g/L Soy bean meal, 15 g/L maltodextrin (Glucidex 6), 5 g/L Bacto peptone. Autoclaved 40 min at 121° C.

MDU-2 medium: 45 g/L maltose, 1 g/L MgSO₄—7 H₂O, 1 g/L NaCl, 2 g/L K₂SO₄, 12 g/L KH₂PO₄, 0.1 ml/L Pluronic 61 L, 0.5 ml/L Trace metal solution. pH 5.0. Autoclaved 20 min at 121° C. 15 ml/L 50% sterile filtered urea is added after autoclaving.

Pectin overlayer gel: 1% HSB agarose, 1% pectin (DE 75%) in a buffer with an appropriate pH. The gel was boiled and then cooled to 55 ° C. before the overlayer was poured onto agar plates.

Transformation of *Aspergillus oryzae* or *Aspergillus niger* (General Procedure)

100 ml of YPD (Sherman et al., Methods in Yeast Genetics, Cold Spring Harbor Laboratory, 1981) is inoculated with spores of A. oryzae or A. niger and incubated with shaking at 37° C. for about 2 days. The mycelium is harvested by filtration through miracloth and washed with 200 ml of 0.6M MgSO₄. The mycelium is suspended in 15 ml of 1.2M MgSO₄. 10 mM NaH₂PO₄, pH=5.8. The suspension is cooled on ice and 1 ml of buffer containing 120 mg of Novozym® 234, batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with .5 ml of 0.6M sorbitol, 100 mM Tris-HCl, pH=7.0. Centrifugation is performed for 15 minutes at 100 g and the protoplasts are collected from the top of the MgSO₄ cushion. 2 volumes of STC (1.2M sorbitol, 10 mM Tris-HCl, pH=7.5. 10 mM CaCl₂) are added to the protoplast suspension and the mixture is centrifuged for 5 minutes at 1000 g. The protoplast pellet is resuspended in 3 ml of STC and repelleted. This is repeated. Finally the protoplasts are resuspended in 0.2–1 ml of STC.

100 µl of protoplast suspension is mixed with 5–25 µg of the appropriate DNA in 10 µl of STC. Protoplasts are mixed with p3SR2 (an A. nidulans amdS gene carrying plasmid). The mixture is left at room temperature for 25 minutes. 0.2 ml of 60% PEG 4000 (BDH 29576). 10 mM $CaCl_2$ and 10 mM Tris-HCl, pH=7.5 is added and carefully mixed (twice) and finally 0.85 ml of the same solution is added and carefully mixed. The mixture is left at room temperature for 25 minutes, spun at 2500. g for 15 minutes and the pellet is resuspended in 2 ml of 1.2M sorbitol. After one more sedimentation the protoplasts are spread on the appropriate plates. Protoplasts are spread on minimal plates (Cove Biochem. Biophys. Acta. 113 (1966) 51–56) containing 1.0M sucrose, pH=7.0, 10mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Fed batch fermentation

Fed batch fermentation was performed in a medium comprising maltodextrin as a carbon source, urea as a nitrogen source and yeast extract. The fed batch fermentation was performed by innoculating a shake flask culture of A. oryzae host cells in question into a medium comprising 3.5% of the carbon source and 0.5% of the nitrogen source. After 24 hours of cultivation at pH 5.0 and 34° C. the continuous supply of additional carbon and nitrogen sources were initiated. The carbon source was kept as the limiting factor and it was secured that oxygen was present in excess. The fed batch cultivation was continued for 4 days, after which the enzymes could be recovered by centrifugation, ultrafiltration, clear filtration and germ filtration.

Purification of the enzyme

The recombinant enzyme from A. oryzae was purified as follows: A culture supernatant was harvested after 5 days of culture, and centrifuged, sterile filtered, and concentrated on a 20 kDa ultrafiltration device to approximately 20% dry matter. 40 ml of this concentrate (containing 80–120 mg rPME) were diluted 10 times in 20 mM Tris pH 8.0 and applied to a HR 16/20 Q-Sepharose fast flow column (Pharmacia, Sweden) at 1.5 ml/min, and eluted with a linear NaCl gradient (from 0 to 0.6M NaCl) at approximately 0.4M NaCl. The fractions containing pectin methyl esterase activity were pooled and ultrafiltrated into 20 mM citrate pH 3.0 and loaded on a HR 16/20 S-Sepharose fast flow column (Pharmacia, Sweden) at 1.5 ml/min, and eluted with a linear NaCl gradient at approximately 0.2M NaCl. The fractions containing PME activity were ultrafiltrated in water and used for characterization as described below. Protein concentrations in the fractions were determined by the Bio Rad protein assay (Bio Rad, USA).

Characterization of an enzyme of the invention

Electrophoresis

SDS-PAGE electrophoresis was performed in a Mini-Leak 4 electrophoresis unit (Kem-En-Tec, Denmark) as a modified version of the Laemli procedure (Laemmli 1970). Isoelectric focusing was carried out on Ampholine PAG plates pH 3.5–9.5 (Pharmacia, Sweden) on a Multiphor electrophoresis unit according to the manufactures instructions. Gels were either silverstained essentially as described in (Merrild, Switzer et al. 1979) or coomassie stained according to (Matsudaira 1989).

pH stat measurements

The equipment used was a titrator TTT80; autoburette ABU80; Titrigraph module REA 160; pH stat unit REA 270 all manufactured by Radiometer, Copenhagen, Denmark. The incubations were done in a 15 ml reactor cell connected to a thermostat and a magnetic stirrer. The reactor was filled with 15 ml 0.2% substrate solution in water, the substrate being apple pectin with a 75% of esterification produced from apple pectin manufactured by Obipektin AG. pH was adjusted to 4.5 with NaOH or HCl (for determination of pH optimum, pH was adjusted to other values as described below), and the temperature of the reaction cell was maintained at 30° C. (except for determination of temperature optimum, as described below). After the enzyme sample had been injected in the reactor, the cell was left stirring for 1 minute, whereafter the reaction was measured over 1.5 minutes. The pH stat injected 10 mM NaOH in the reactor cell to maintain constant pH, and the number of hydrolyzed methyl ester linkage (hmel) is directly proportional to the amount of NaOH injected into the reactor according to the following equation:

$$n(hmel)=n(NaOH)(1+[H+]/Ka*))$$

*) The $pK_a$ of galacturonic acid is approximately 3.5 at 30° C.

Determination of pH optimum

The experiments were conducted at pH values varying from 2.5–6.0. 1.5 µg of purified enzyme in a volume of 50 ml were added to the solution and measurements carried out as described above. The activity was expressed as percentage of the maximal activity (pH 4.55).

Determination of pH stability

For determination of pH stability, 1.5 µg of enzyme in a volume of 50 ml were added to 10 ml 0.1% substrate solution in the reactor cell, and the pH adjusted to a value between 2.5 and 8. After 1 hour incubation at 30° C., 5 ml 0.4% substrate solution were added and pH adjusted to 4.5. Subsequently activity measurements were carried out as described above.

Determination of temperature optimum

The experiments were conducted at temperature values varying from 25°–62° C. 1.5 µg of purified enzyme in a volume of 50 ml were added to the solution and measurements carried out as described above. The activity was expressed as percentage of the maximal activity (43° C.).

Determination of temperature stability

The enzyme samples were incubated at various temperatures between 30° and 80° for 0.1 and 2 hours, after which the activity was measured as described above.

Determination of pectin methylesterase activity 1 unit of pectin methyl esterase activity (PMEU) is defined as the amount of pectin methyl esterase which hydrolyzes 1 µmole of pectin methyl ester per minute with citrus pectin (72% methylation) as the substrate at 0.5% by weight substrate concentration at pH 4.8 and 22° C.

EXAMPLE 1

A library from A. aculeatus consisting of approx. $1.5 \times 10^6$ individual clones in 150 pools was constructed.

DNA was isolated from 20 individual clones from the library and subjected to analysis for cDNA insertion. The insertion frequency was found to be >90% and the average insert size was approximately 1400 bp.

DNA from some of the pools was transformed into yeast, and 50–100 plates containing 200–500 yeast colonies were obtained from each pool. After 3–5 days of growth, the agar plates were replica plated onto several sets of agar plates.

One set of plates was then incubated for 2–4 days at 30° C. and overlayered with a pectin overlayer gel for detection of pectinolytic activity. After incubation overnight at 30° C., 10–15 ml of a 1% solution of MTAB (mixed alkyltrimethylammonium bromide) was poured onto the overlayer and removed after 1 hour. PME positive colonies were identified as colonies surrounded by a white halo.

Cells from enzyme-positive colonies were spread for single colony isolation on agar, and an enzyme-producing single colony was selected for each of the PME-producing colonies identified.

Characterization of positive clones: The positive clones were obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al., 1977) and the Sequenase system (United States Biochemical). The cDNA sequence encoding the enzyme is shown in SEQ ID no. 1.

Isolation of a cDNA gene for expression in Aspergillus

One or more of the PME-producing colonies were inoculated into 20 ml YNB-1 broth in a 50 ml glass test tube. The tube was shaken for 2 days at 30° C. The cells were harvested by centrifugation for 10 min. at 3000 rpm.

The cells were resuspended in 1 ml 0.9M sorbitol, 0.1M EDTA, pH 7.5. The pellet was transferred to an Eppendorf tube, and spun for 30 seconds at full speed. The cells were resuspended in 0.4 ml 0.9M sorbitol, 0.1M EDTA, 14 mM β-mercaptoethanol. 100 µl 2 mg/ml Zymolase was added, and the suspension was incubated at 37° C. for 30 minutes and spun for 30 seconds. The pellet (spheroplasts) was resuspended in 0.4 ml TE. 90 µl of (1.5 ml 0.5M EDTA pH 8.0, 0.6 ml 2M Tris-Cl pH 8.0, 0.6 ml 10% SDS) was added, and the suspension was incubated at 65° C. for 30 minutes. 80 µl 5M KOAc was added, and the suspension was incubated on ice for at least 60 minutes and spun for 15 minutes at full speed. The supernatant was transferred to a fresh tube which was filled with EtOH (room temp.) followed by thorough but gentle mixing and spinning for 30 seconds. The pellet was washed with cold 70% ETOH, spun for 30 seconds and dried at room temperature. The pellet was resuspended in 50 µl TE and spun for 15 minutes. The supernatant was transferred to a fresh tube. 2.5 µl 10 mg/ml RNase was added, followed by 5 incubation at 37° C. for 30 minutes and addition of 500 µl isopropanol with gentle mixing. The mixture was spun for 30 seconds, and the supernatant was removed. The pellet was rinsed with cold 96% EtOH and dried at room temperature. The DNA was dissolved in 50 µl water to a final concentration of approximately 100 µl/ml.

The DNA was transformed into *E. coli* by standard procedures. Two *E. coli* colonies were isolated from each of the transformations and analysed with the restriction enzymes HindIII and XbaI which excised the DNA insert. DNA from one of these clones was retransformed into yeast strain JG169.

The DNA sequences of several of the positive clones were determined. The entire DNA sequence of a PME is shown in SEQ ID No. 1, a partial DNA sequence is shown in SEQ ID No. 3.

EXAMPLE 2

In order to express the genes in Aspergillus, cDNA is isolated from one or more representatives of each family by digestion with HindIII/XbaI or other appropriate restriction enzymes, size fractionation on a gel and purification and subsequently ligated to pHD414, resulting in the plasmid pA1PE1.2. After amplification in *E. coli*, the plasmids are transformed into *A. oryzae* or *A. niger* according to the general procedure described above.

Test of *A. oryzae* transformants

Each of the transformants was inoculated in the center of a Petri dish with FG-4 agar. After 5 days of incubation at 30° C. 4 mm diameter plugs were removed from the center of the colonies by a corkscrew. The plugs were embedded in a pectin overlayer gel and incubated overnight at 40° C. The PME activity was identified as described above. Some of the transformants had halos which were significantly larger than the *A. oryzae* background. This demonstrates efficient expression of PME in *A. oryzae*. The 8 transformants with the highest PME activity were selected and inoculated and maintained on YPG-agar.

Each of the 8 selected transformants were inoculated from YPG-agar slants on 500 ml shake flask with FG-4 and MDU-2 media. After 3–5 days of fermentation with sufficient agitation to ensure good aeration, the culture broths were centrifuged for 10 minutes at 2000 g and the supernatants were analyzed.

A volume of 15 µl of each supernatant was applied to 4 mm diameter holes punched out in a pectin overlayer gel (25 ml in a 13 cm diameter Petri dish). The PME activity was identified by the formation of a white halo on incubation.

Subsequently, the PME was produced by fed batch fermentation of *A. oryzae* expressing the enzyme as described in Materials and Methods above.

EXAMPLE 3

Purification and characterization of a cloned recombinant PME of the invention

PME hydrolyzes the ester-linkage between methanol and galacturonic acid in esterified pectin. Hence, the action of the enzyme can be measured by the decrease in pH which happens concomitant with the formation of free acid groups. This analysis method has been used for determination of Km, Vmax, pH & Temperature optimum of a PME of the invention as well as determination of how temperature, pH and substrate concentration affects the activity of the enzyme.

Purification of the enzyme

The purification of a recombinant enzyme from *A. oryzae* produced as described above was purified and characterized by the methods described in the Materials and Methods section above. The following results were obtained:

The molecular weight of the enzyme was determined to 43 kD by SDS-PAGE. This is higher than the calculated molecular weight of the enzyme (approx. 35 kD) indicating that the enzyme may be glycosylated to a significant extent. The isoelectric point was determined to 3.8 by isoelectric focusing, which is slightly lower than the calculated value (4.1). This may also indicate that the enzyme undergoes a significant post-translational processing (e.g. glycosylation).

The pH optimum was measured to approximately pH 4.5 (FIG. 3) and the temperature optimum to 45° C. (FIG. 4). the activity drops sharply at pH above 4.5 and temperatures above 50° C., whereas the drop in activity at lower temperatures and pH was less pronounced. The special method of measuring pH stability precludes an exact measurement of pH sensitivity of the enzyme, but the PME of the invention appears to be most stable at neutral pH, i.e. above 5.5–6 such as within pH 6–8 (FIG. 5). The enzyme was relatively sensitive to elevated temperatures, i.e. temperatures above 50° C. Already after 1 hour at 50°, almost 80% of the activity has been lost (FIG. 6).

Finally, the reaction speed, $V_{max}$, and $K_M$ was determined for the enzyme by varying the substrate concentration during incubation, and plot the results in a Hanes plot, where $[S]/V=[S] 1/V_{max}+K_m/V_{max}$ (FIG. 7). $K_m$ was measured to 2.8% on 75% esterified apple pectin (apple pectin, with a 75% degree of esterification). This is a relatively high value, which indicates a relatively low affinity to the substrate. The maximal velocity of the enzyme, $V_{max}$, was determined to 8.6 µmol/min, and the specific activity was determined to 5.5 mmol/(min/mg).

When using citruc pectin (DE=70–72%) as a substrate and performing the assay at a temperature of 22° C., the Km was determined to be 0.5%, the Vmax to 6.0 µmol/min, and the specific activity was determined to 239 µmol/(min/mg). Furthermore, under these conditions the pH optimum was determined to approx. 4.8.

The enzyme was not able to hydrolyze acetyl-ester groups from neither acetylated polysaccharides, nor the synthetic acetyl-esterase substrate p-nitro-phenol-acetate, demonstrating its substrate specificity. The specific activity on apple pectin of 5.5 mmol/(min/mg) indicates that the enzyme has a very high catalytic capacity.

As expected the enzyme has a significant synergistic effect on pectin degradation when used in combination with polygalacturonases. By incubation with an A. aculeatus polygalacturonase (PCT/DK93/00445) with or without PME of the invention it was found that polygalacturonase alone has only limited activity towards the pectin, PME alone has no effect on the degradation of the pectin, but the use of PME in combination with polygalacturonase significantly increases the substrate degrading capability of the polygalacturonase whereby oligomeric material is formed.

The acidic pH optimum of the enzyme indicates that it may be of great value in fruit juice processing where the pH frequently is below pH 5.0, but it may also be of use in the wine, feed and food industry, where pectin containing plant material is processed.

EXAMPLE 4

Demethylation of pectin 40.0 g of pectin having a degree of esterification of 72% were diluted in 2000 mls, 80° C. demineralized water. The pectin solution was tempered to 30° C., pH was adjusted to 4.5 with 0 25M NaHCO₃.

34 PMEU/g pectin of PME produced as described above were added to 2000 mls of pectin solution. At the time 10, 30, 60, 120, 180 min., 50 mls samples were taken out and heat treated to inactivate the enzyme (100° C., 10 min.). Afterwards, the samples were analysed in accordance with the following method:

6.25 g of the 2% enzyme treated solutions was added and dissolved in 1.25 ml ethanol and 25 ml $CO_2$-free demineralized water. The amount of free carboxyl groups is determined by titration with 0.2M NaOH to the equivalence point (pH 7.0) to determine the nonesterified galacturonic acid units. A known excess of aqueous NaOH was added and saponification was allowed to take place for 1 hour. Then, an equivalent amount of HCl was added and the sample was again titrated to pH 7.0 to determine the amount of esterified galacturonic acid units. The degree of esterification, DE %, was then calculated.

The results are apparent from the table below:

| Time, min. | 0    | 10 | 30 | 60 | 120 | 180 |
|------------|------|----|----|----|-----|-----|
| DE %       | (72)* | 52 | 39 | 33 | 27  | 26  |

*not measured.

EXAMPLE 5

Orange marmalade

Oranges were washed and minced in a meat chopping machine. The fruit was added sugar in the level fruit/sugar: ⅗ based on weight. Then the fruit mass was cooked for about 15 min and cooled to −18° C.

The fruit mass was later diluted 1:1 by demineralized water, tempered to 40° C. and pectin methyl esterase prepared as described above was added to 50 g samples in amounts of 17, 1.7 and 0.17 PMEU/g of pectin. The pH of the samples remained unadjusted 3.5. The pectin was estimated to be 30% w/w of the fruit. A control was also prepared, consisting of 17 PMEU/g of pectin (inactivation 85° C. for 3 minutes). The reaction time was 1 hour.

The samples were then cooled to 4° C. over night and the following day the hardness of the gels was evaluated at 4° C., before and after a heat treatment (85° C. for 3 min) of the samples.

The measurement of the hardness of the gels was carried out by using SMS Texture Analyser. The conditions of the texture analysis were as follows:

| Probe, diameter mm: | 20 |
| Penetration: | 20% |
| Rate: | 2 mm/sek |

The hardness, N, appears from below:

|  | 17 PMEU/g N | 1.7 PMEU/g N | 0.17 PMEU/g N | contro l N |
|---|---|---|---|---|
| Before inactivation | 5.24 | 2.11 | 0.26 | 0.08 |
| After inactivation | 3.97 | 1.52 | 0.26 | 0.09 |

EXAMPLE 6

Tomato paste

Canned, peeled plum tomatoes added tomato juice and citric acid, bought at the grossery store were used as a substrate for the following PME-trials.

Pectin methyl esterase prepared as described above was added to a portion of 100 g in an amount of 5 PMEU/g tomato product, a control was added 5 PMEU of inactivated PME/g tomato product. The samples were mixed and left for 40° C. for 30 minutes. The samples were then placed at 4° C. until the next day and measured by SMS Texture Analyser at 17° C. The samples were heat treated for 85° C. in 3 min to inactivate the enzyme and after having adjusted the temperature to 17° C., the samples were again measured by SMS Texture Analyser.

The texure analyser measures the hardness, N. The probe is a 20 mm probe, penetration of the sample was 20%, the speed was 2 mm/sek.

pH of both the control and the test sample was 4.4. The results are apparent from the table below.

|  | Hardness, N before inactivation | Hardness, N after inactivation |
|---|---|---|
| test sample | 0.31 | 0.24 |
| control | 0.09 | 0.10 |

EXAMPLE 6

Pudding-Like Milk Dessert 198 g of milk was heated to 80° C. in a microwave oven. 2 g of rapid set HM pectin was added at 80° C. by vigerous mixing. The milk was afterwards tempered to 30° C. and pectin methyl esterase prepared as described above was added to 100 ml of the mixture in an amount of 5 PMEU/ml. A 100 ml control was also prepared containing the same amount of inactivated enzyme (85° C. in 3 min). The pH of the two samples was 6.3.

The test sample containing active enzyme gelled in 10 min while the control remained fluent.

REFERENCES

Aviv, H. & Leder, P. 1972. Proc. Natl. Acad. Sci. U.S.A. 69: 1408–1412.

Becker, D. M. & Guarante, L. 1991. Methods Enzymol. 194: 182–187.

Chirgwin, J. M., Przybyla, A. E., MacDonald, R. J. & Rutter, W. J. 1979. Biochemistry 18: 5294–5299.

Gubler, U. & Hoffman, B. J. 1983. Gene 25: 263–269.

Sambrook, J., Fritsch, E. F. & Maniatis, T. 1989. Molecular Cloning: A Laboratory Manual. Cold Spring Harbor Lab., Cold Spring Harbor, N.Y.

Sanger, F., Nicklen, S. & Coulson, A. R. 1977. Proc. Natl. Acad. Sci. U.S. A. 74: 5463–5467.

van Rijssel et al., Applied and Environmental Microbiology, Mar. 1993, pp 828–836.

Khanh et al., Nucleic Acids Reserch, vol. 18, No. 14, 1990.

Q. Khanh et al., Biotechnology Letters, Vol. 14, No. 11 (Nov. 1992) pp. 1047–1052.

Markovic and Jornwall, Protein Science (1992), I, 1288–1292. Cambridge University Press.

We claim:

1. An enzyme exhibiting pectin methylesterase activity, wherein the enzyme
   a) is derived from *Aspergillus aculeatus*;
   b) is encoded by the coding part of the DNA sequence of SEQ ID No: 1; or
   c) has the amino acid sequence of SEQ ID No: 2 or a sequence which is at least 95% homologous thereto.

2. An enzyme exhibiting pectin methylesterase activity, which enzyme is encoded by a DNA sequence comprising the following partial sequence

```
TAAAGAGTCG ATCATACACT CATATCAATC GCAAAAATGG TTAAATCAGT CTTGGCTTCC      (SEQ ID NO: 3)
GCTCTCTTCG CCGCGTCCGC ACTGGCTGCC AGCCGTACCA CGGCTCCCTC CGGCGCGATC
GTCGTCGCCA AGTCTGGTGG TGACTATACC ACTATTGGTG ATGCCATTGA TGCTCTGAGC
ACCAGCACCA CCGACACCCA AACCATTTTC ATCGAGGAGG GTACCTACGA TGAGCAGGTC
TACCTGCCTG CTATGACCGG CAAGGTCATC ATCTACGTCA AACCGAGAAC ACCGACTCCT
ACG
```

3. The enzyme of claim 1, which has one or more of the following properties:
   (a) a pH optimum of 4.5 as determined at 30° C. using 75% esterified pectin as a substrate;
   (b) a temperature optimum of 45° C. as determined using 75% esterified pectin as a substrate; and
   (c) a molecular weight of 43 kD determined by SDS-PAGE.

4. The enzyme of claim 1, wherein the enzyme is derived from a microorganism.

5. The enzyme of claim 4, wherein the enzyme is derived from a filamentous fungus or a yeast.

6. The enzyme of claim 5, wherein the enzyme is derived from a strain of Aspergillus, Trichoderma, Penicillium, Fusarium or Humicola.

7. The enzyme of claim 6, wherein the enzyme is derived from a strain of Aspergillus.

8. The enzyme of claim 7, *Aspergillus aculeatus* has the accession number CBS 101.43.

9. An enzyme preparation useful for the modification of plant cell wall components, said preparation comprising the enzyme of claim 1.

10. The preparation of claim 9, which additionally comprises one or more other plant cell wall degrading enzymes selected from the group consisting of pectin lyase, pectate lyase, arabinanase, xylanase, glucanase, galactanase, marmanase, rhamnogalacturonase, rhamnogalacturonan acetylesterase, pectin acetylesterase, polygalacmronase and pectin methylesterase.

11. The enzyme of claim 7, wherein the Aspergillus strain is one of *Aspergillus aculeatus*, *Aspergillus niger* or *Aspergillus oryzae*.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 1195 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AGTCGATCAT ACACTCATAT CAATCGCAAA AATGGTTAAA TCAGTCTTGG CTTCCGCTCT    60
CTTCGCCGTG TCCGCACTGG CTGCCAGCCG TACCACGGCT CCCTCCGGCG CGATCGTCGT   120
CGCCAAGTCT GGTGGTGACT ATACCACTAT TGGTGATGCC ATTGATGCTC TGAGCACCAG   180
CACCACCGAC ACCCAAACCA TTTTCATCGA GGAGGGTACC TACGATGAGC AGGTCTACCT   240
GCCTGCTATG ACCGGCAAGG TCATCATCTA CGGTCAAACC GAGAACACCG ACTCCTACGC   300
CGACAACCTG GTCACCATCA CCCACGCCAT CAGCTACGAG GATGCTGGTG AGAGCGATGA   360
TCTGACTGCT ACCTTCCGCA ACAAGGCTGT CGGCTCTCAG GTCTACAACC TCAACATTGC   420
CAACACCTGT GGTCAGGCTT GCCACCAGGC TTTGGCCTTG TCCGCCTGGG CTGACCAGCA   480
GGGTTACTAC GGCTGCAACT TCACTGGTTA CCAGGATACC CTCCTCGCTC AGACCGGTAA   540
CCAGCTCTAC ATCAACTCCT ACATTGAGGG TGCTGTCGAC TTCATCTTTG GCCAGCACGC   600
TCGTGCTTGG TTCCAGAACG TCGACATCCG TGTCGTTGAG GGTCCTACCT CTGCCTCCAT   660
CACCGCCAAC GGCCGCTCCT CCGAGACTGA CACCTCCTAC TACGTGATCA ACAAGTCGAC   720
CGTTGCTGCT AAGGAGGGCG ACGACGTTGC CGAAGGCACC TACTACCTTG GCCGCCCCTG   780
GTCCGAGTAC GCCCGTGTCG TCTTCCAGCA GACCAGCATG ACCAACGTCA TCAACTCCCT   840
CGGCTGGACT GAGTGGTCCA CCTCCACCCC TAACACCGAG TACGTCACCT TCGGCGAGTA   900
CGCCAACACC GGCGCCGGCT CCGAGGGCAC CCGCGCCAGC TTCGCCGAGA AGCTGGATGC   960
CAAGCTCACC ATCACGGATA TCCTGGGCTC TGACTACACC AGCTGGGTCG ATACCTCCTA  1020
```

```
CTTCTAAGCT GGACGCATGA GTAGTTGTTA AGAATGCGTG AGATGGCTGT CAACCAACAG    1080

CAGAGCTGAC CGTATGCGGT GCATATACTT TTCTCTTCGT CAAATAATTT CCCTTTGATA    1140

AAGCAATTTA ATTGGCATGC ACAGTCCATG CTTGACACAA AAAAAAAAAA AAAAA          1195
```

( 2 ) INFORMATION FOR SEQ ID NO:2:

( i ) SEQUENCE CHARACTERISTICS:
        ( A ) LENGTH: 331 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Met Val Lys Ser Val Leu Ala Ser Ala Leu Phe Ala Val Ser Ala Leu
 1               5                  10                  15

Ala Ala Ser Arg Thr Thr Ala Pro Ser Gly Ala Ile Val Ala Lys
            20                  25                  30

Ser Gly Gly Asp Tyr Thr Thr Ile Gly Asp Ala Ile Asp Ala Leu Ser
            35                  40                  45

Thr Ser Thr Thr Asp Thr Gln Thr Ile Phe Ile Glu Glu Gly Thr Tyr
 50                  55                  60

Asp Glu Gln Val Tyr Leu Pro Ala Met Thr Gly Lys Val Ile Ile Tyr
 65                  70                  75                  80

Gly Gln Thr Glu Asn Thr Asp Ser Tyr Ala Asp Asn Leu Val Thr Ile
                 85                  90                  95

Thr His Ala Ile Ser Tyr Glu Asp Ala Gly Glu Ser Asp Asp Leu Thr
             100                 105                 110

Ala Thr Phe Arg Asn Lys Ala Val Gly Ser Gln Val Tyr Asn Leu Asn
             115                 120                 125

Ile Ala Asn Thr Cys Gly Gln Ala Cys His Gln Ala Leu Ala Leu Ser
     130                 135                 140

Ala Trp Ala Asp Gln Gln Gly Tyr Tyr Gly Cys Asn Phe Thr Gly Tyr
 145                 150                 155                 160

Gln Asp Thr Leu Leu Ala Gln Thr Gly Asn Gln Leu Tyr Ile Asn Ser
                 165                 170                 175

Tyr Ile Glu Gly Ala Val Asp Phe Ile Phe Gly Gln His Ala Arg Ala
             180                 185                 190

Trp Phe Gln Asn Val Asp Ile Arg Val Val Glu Gly Pro Thr Ser Ala
             195                 200                 205

Ser Ile Thr Ala Asn Gly Arg Ser Ser Glu Thr Asp Thr Ser Tyr Tyr
     210                 215                 220

Val Ile Asn Lys Ser Thr Val Ala Ala Lys Glu Gly Asp Asp Val Ala
 225                 230                 235                 240

Glu Gly Thr Tyr Tyr Leu Gly Arg Pro Trp Ser Glu Tyr Ala Arg Val
                 245                 250                 255

Val Phe Gln Gln Thr Ser Met Thr Asn Val Ile Asn Ser Leu Gly Trp
             260                 265                 270

Thr Glu Trp Ser Thr Ser Thr Pro Asn Thr Glu Tyr Val Thr Phe Gly
             275                 280                 285

Glu Tyr Ala Asn Thr Gly Ala Gly Ser Glu Gly Thr Arg Ala Ser Phe
     290                 295                 300

Ala Glu Lys Leu Asp Ala Lys Leu Thr Ile Thr Asp Ile Leu Gly Ser
 305                 310                 315                 320

Asp Tyr Thr Ser Trp Val Asp Thr Ser Tyr Phe
                 325                 330
```

( 2 ) INFORMATION FOR SEQ ID NO:3:

( i ) SEQUENCE CHARACTERISTICS:
        ( A ) LENGTH: 303 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
TAAAGAGTCG ATCATACACT CATATCAATC GCAAAAATGG TTAAATCAGT CTTGGCTTCC      60
GCTCTCTTCG CCGCGTCCGC ACTGGCTGCC AGCCGTACCA CGGCTCCCTC CGGCGCGATC     120
GTCGTCGCCA AGTCTGGTGG TGACTATACC ACTATTGGTG ATGCCATTGA TGCTCTGAGC     180
ACCAGCACCA CCGACACCCA AACCATTTTC ATCGAGGAGG GTACCTACGA TGAGCAGGTC     240
TACCTGCCTG CTATGACCGG CAAGGTCATC ATCTACGTCA AACCGAGAAC ACCGACTCCT     300
ACG                                                                   303
```

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
TAAAGAGTCG ATCATACACT                                                  20
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
CATATCAATC GCAAAAATGG                                                  20
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

```
TTAAATCAGT CTTGGCTTCC                                                  20
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (ii) MOLECULE TYPE: cDNA (xi) SEQUENCE DESCRIPTION: SEQ ID NO:7:

GCTCTCTTCG CCGCGTCCGC                 20

(2) INFORMATION FOR SEQ ID NO:8:

(i) SEQUENCE CHARACTERISTICS:
   (A) LENGTH: 20 base pairs
   (B) TYPE: nucleic acid
   (C) STRANDEDNESS: single
   (D) TOPOLOGY: linear (ii) MOLECULE TYPE: cDNA (xi) SEQUENCE DESCRIPTION: SEQ ID NO:8:

ACTGGCTGCC AGCCGTACCA                 20

(2) INFORMATION FOR SEQ ID NO:9:

(i) SEQUENCE CHARACTERISTICS:
   (A) LENGTH: 20 base pairs
   (B) TYPE: nucleic acid
   (C) STRANDEDNESS: single
   (D) TOPOLOGY: linear (ii) MOLECULE TYPE: cDNA (xi) SEQUENCE DESCRIPTION: SEQ ID NO:9:

CGGCTCCCTC CGGCGCGATC                 20

(2) INFORMATION FOR SEQ ID NO:10:

(i) SEQUENCE CHARACTERISTICS:
   (A) LENGTH: 20 base pairs
   (B) TYPE: nucleic acid
   (C) STRANDEDNESS: single
   (D) TOPOLOGY: linear (ii) MOLECULE TYPE: cDNA (xi) SEQUENCE DESCRIPTION: SEQ ID NO:10:

GTCGTCGCCA AGTCTGGTGG                 20

(2) INFORMATION FOR SEQ ID NO:11:

(i) SEQUENCE CHARACTERISTICS:
   (A) LENGTH: 20 base pairs
   (B) TYPE: nucleic acid
   (C) STRANDEDNESS: single
   (D) TOPOLOGY: linear (ii) MOLECULE TYPE: cDNA (xi) SEQUENCE DESCRIPTION: SEQ ID NO:11:

TGACTATACC ACTATTGGTG                 20

(2) INFORMATION FOR SEQ ID NO:12:

(i) SEQUENCE CHARACTERISTICS:
   (A) LENGTH: 20 base pairs
   (B) TYPE: nucleic acid
   (C) STRANDEDNESS: single
   (D) TOPOLOGY: linear (ii) MOLECULE TYPE: cDNA (xi) SEQUENCE DESCRIPTION: SEQ ID NO:12:

ATGCCATTGA TGCTCTGAGC                 20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

ACCAGCACCA CCGACACCCA         20

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

AACCATTTTC ATCGAGGAG         19

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

GGTACCTACG ATGAGCAGG         19

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

TCTACCTGCC TGCTATGACC         20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GGCAAGGTCA TCATCTACGT         20

( 2 ) INFORMATION FOR SEQ ID NO:18:

( i ) SEQUENCE CHARACTERISTICS:

( A ) LENGTH: 25 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:18:

CAAACCGAGA ACACCGACTC CTACG 25